(12) United States Patent
Schiff et al.

(10) Patent No.: US 8,858,582 B2
(45) Date of Patent: Oct. 14, 2014

(54) PUSH ACTIVATION LANCET DEVICE

(75) Inventors: David R. Schiff, Highland Park, NJ (US); Peter Byar, Willingboro, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1967 days.

(21) Appl. No.: 11/400,726

(22) Filed: Apr. 7, 2006

(65) Prior Publication Data
US 2006/0259058 A1    Nov. 16, 2006

Related U.S. Application Data

(60) Provisional application No. 60/669,249, filed on Apr. 7, 2005.

(51) Int. Cl.
*A61B 17/32* (2006.01)
*A61B 5/151* (2006.01)
*A61B 5/15* (2006.01)

(52) U.S. Cl.
CPC ........... *A61B 5/1411* (2013.01); *A61B 5/1433* (2013.01); *A61B 5/15142* (2013.01)
USPC ...................................................... 606/181

(58) Field of Classification Search
USPC .................................. 606/182, 181; 600/583
See application file for complete search history.

(56) References Cited

U.S. PATENT DOCUMENTS

| | | | | |
|---|---|---|---|---|
| 4,203,446 A * | 5/1980 | Hofert et al. | | 606/182 |
| 4,388,925 A | 6/1983 | Burns | | |
| 4,624,253 A * | 11/1986 | Burns | | 606/181 |
| 4,653,513 A * | 3/1987 | Dombrowski | | 600/578 |
| 4,677,979 A | 7/1987 | Burns et al. | | |
| 5,356,420 A * | 10/1994 | Czernecki et al. | | 606/182 |
| 5,421,347 A * | 6/1995 | Enstrom | | 600/567 |
| 5,611,809 A | 3/1997 | Marshall et al. | | |
| 5,755,733 A * | 5/1998 | Morita | | 606/182 |
| 6,053,930 A * | 4/2000 | Ruppert | | 606/181 |
| 6,248,120 B1 | 6/2001 | Wyszogrodzki | | |
| 6,432,120 B1 | 8/2002 | Teo | | |
| 6,613,064 B2 * | 9/2003 | Rutynowski et al. | | 606/185 |
| 6,852,119 B1 | 2/2005 | Abulhaj et al. | | |
| 7,175,641 B1 * | 2/2007 | Schraga | | 606/181 |
| 2002/0087180 A1 * | 7/2002 | Searle et al. | | 606/181 |
| 2006/0052809 A1 | 3/2006 | Karbowniczek | | |
| 2006/0129173 A1 | 6/2006 | Wilkinson | | |

FOREIGN PATENT DOCUMENTS

GB    2352403 A    1/2001

* cited by examiner

*Primary Examiner* — Thomas McEvoy
*Assistant Examiner* — Julie A Szpira
(74) *Attorney, Agent, or Firm* — The Webb Law Firm

(57) ABSTRACT

A lancet device including a lancet having a puncturing element disposed within a two-piece housing including a rear housing and a forward housing. Relative axial movement of the rear housing toward the forward housing directly drives the lancet to a puncturing position wherein the puncturing element extends through the forward housing. During such relative axial movement, a drive structure applies a driving force against the lancet and disengages from the lancet based on deflecting structure in the housing, thereby releasing the driving force applied to the lancet. A retention member then retracts the lancet back within the housing, with the drive structure maintained disengaged from the lancet to prevent re-use.

17 Claims, 14 Drawing Sheets

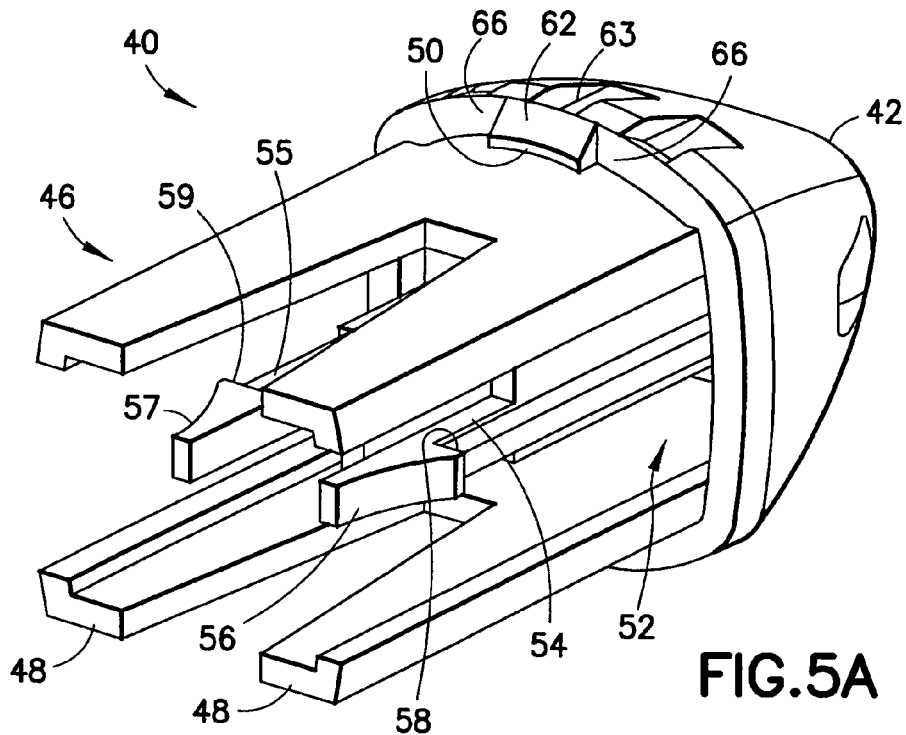
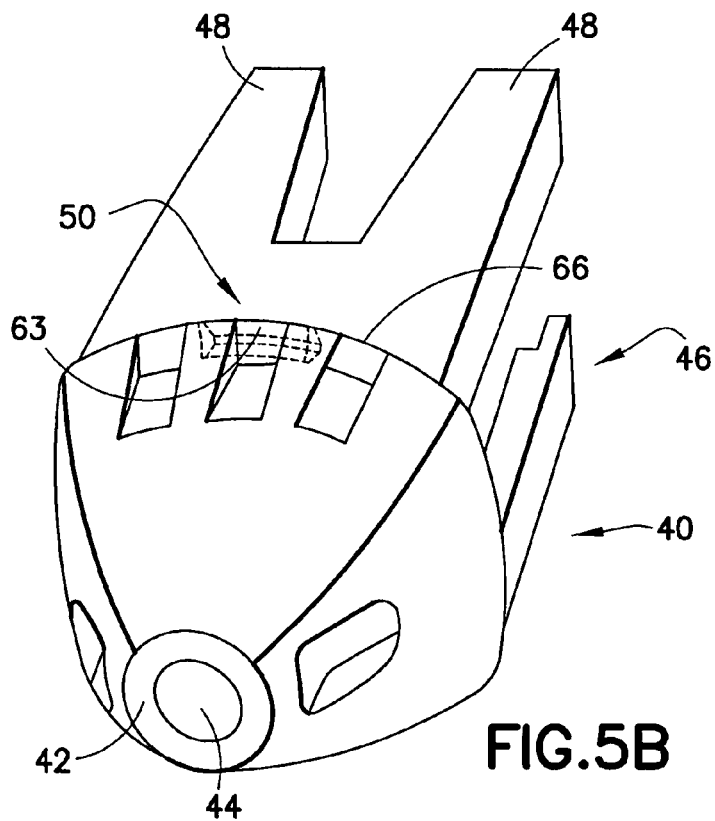

PUSH ACTIVATION LANCET DEVICE

The present application claims the benefit of U.S. Provisional Patent Application No. 60/669,249 as filed on Apr. 7, 2005.

BACKGROUND OF THE INVENTION

1. Field of the Invention

The present invention relates generally to medical puncturing devices, commonly referred to as lancets, which are used to take blood samples from patients.

2. Description of Related Art

Lancet devices are used in the medical field for puncturing the skin of a patient to obtain a capillary blood sample from the patient. Certain diseases, such as diabetes, require that the patient's blood be tested on a regular basis to monitor, for example, the patient's blood sugar levels. Additionally, test kits, such as cholesterol test kits, often require a blood sample for analysis. The blood collection procedure usually involves pricking a finger or other suitable body part in order to obtain the blood sample. Typically, the amount of blood needed for such tests is relatively small and a small puncture wound or incision normally provides a sufficient amount of blood for these tests.

Various lancet devices are commercially available to hospitals, clinics, doctors' offices, and the like, as well as to individual consumers. Such devices typically include a sharp-pointed member such as a needle, or a sharp-edged member such as a blade, that is used to make a quick puncture wound or incision in the patient's skin in order to provide a small outflow of blood. It is often physiologically and psychologically difficult for many people to prick their own finger with a hand-held needle or blade. As a result, lancet devices have evolved into automatic devices that puncture or cut the skin of the patient upon the actuation of a triggering mechanism. In some devices, the needle or blade is kept in a standby position until it is triggered by the user, who may be a medical professional in charge of drawing blood from the patient, or the patient himself or herself. Upon triggering, the needle or blade punctures or cuts the skin of the patient, for example on the finger. Often, a spring is incorporated into the device to provide the "automatic" force necessary to puncture or cut the skin of the patient.

It is of the utmost importance in the medical field that such medical puncturing devices or lancets are in a sterile condition before use. Today, generally without exception, medical puncturing devices or lancets are manufactured and packaged in a sterilized condition before they are distributed to medical professionals and members of the public who have a need for such devices. The sterile packaging maintains the sterility of the device, ensuring that the surrounding environment does not contaminate it until use. In addition, it is also of increasing importance that the user or another person does not come into contact with the needle or blade after use of the device. With the concern over blood-borne diseases, medical professionals are required to take great care with medical devices that come into contact with the blood of patients. Thus, an important aspect of lancet design involves preventing the needle or blade of the device from wounding the user or another person after the blood sample is drawn from the patient. Once used, the needle or blade should be shielded to prevent the needle or blade from wounding the user or another person handling the device. Moreover, the lancet device should be disposable to eliminate the chances of disease transmission due to the needle or blade being used on more than one person. In this regard, the lancet device should ideally be designed for one firing, and have safety features to prevent reuse.

Advances have been made in recent years to increase safety in operating and handling used lancet devices. For example, lancet devices are currently available which are single shot devices that feature automatic ejection and retraction of the puncturing or cutting element from and into the device. Examples of such medical puncturing devices are disclosed in U.S. Pat. Nos. 5,755,733; 6,432,120; and 6,248,120. U.S. Pat. No. 5,755,733 to Morita discloses a lancet device that includes a combined holder and lancet structure with a compressible spring member that causes a lancet member to puncture the skin of a patient upon actuation of a pair of actuating arms. U.S. Pat. No. 6,432,120 to Teo discloses a lancet device including a lancet holder which contains a spring-loaded lancet structure with a single spring that effects the ejection and retraction of a lancet needle upon triggering of the structure. U.S. Pat. No. 6,248,120 to Wyszogrodzki discloses a lancet device comprised of a housing, a shielding portion, a piston with a puncturing tip, and separate drive and return springs that eject and retract the piston, respectively, upon the breakage of internal wing elements in the housing. Such assemblies include many components, and oftentimes utilize costly metal coil springs for activation.

As an alternative to spring activated lancets, U.S. Pat. No. 6,053,930 discloses a lancet assembly which involves a driving assembly including a plurality of interengaging parts for applying pressure by the user to cause the puncturing tip to pierce the skin, with a spring member attached to a cover over the forward end of the device for retracting the lancet within the body after use. Such a device relies on the specific profile design of the housing and the lancet in order to retract the lancet, and includes a plurality of interengaging parts, increasing manufacturing and assembly costs.

SUMMARY OF THE INVENTION

A need generally exists in the medical field for a simple, reliable, and disposable medical puncturing device that is easy to manufacture, assemble and use, and which ensures sterility before use and enables safe and secure disposal after use.

In accordance with an embodiment of the invention, a lancet device comprises a housing including a first housing portion and a second housing portion axially or longitudinally movable with respect to each other, and a lancet structure having a puncturing element retained within the housing. The first housing portion includes a drive structure for abutting engagement with a corresponding surface of the lancet structure. The second housing portion includes a guiding surface adapted for engagement with the drive structure of the first housing portion during axial movement of the first housing portion and the second housing portion with respect to each other. The puncturing element of the lancet structure is maintained within the housing by a lancet retention member. Axial movement of the first housing portion with respect to the second housing portion directly and momentarily positions the lancet structure in a position wherein the puncturing element extends through a forward end of the second housing portion due to the abutting engagement between the drive structure and the lancet structure. Such axial movement also causes the drive structure to engage the guiding surface of the second housing portion, thereby disengaging the drive structure from the abutment surface of the lancet upon extension of the puncturing element through the forward end of the second housing portion. Disengaging the drive surface from the abutment surface permits the lancet retention member to retract the puncturing element within the forward end of the second housing portion.

In one embodiment, the lancet retention member comprises at least one, and desirably a pair, of leaf springs biasing the lancet structure away from the forward end of the first housing portion. The leaf spring may be integrally formed with the lancet structure.

The drive structure may be in the form of one or more resiliently flexible fingers having one or more protrusions for interference engagement with an abutment surface of the lancet structure. Moreover, the guide surface of the second housing portion may include a ramped surface having a notch for interference engagement with the protrusion of the drive structure upon axial movement of the first housing portion and the second housing portion toward each other. In this manner, the drive structure can be maintained in a position in which it is disengaged from the abutment surface of the lancet structure after the drive structure forces the puncturing element to a piercing position and is retracted into the housing, thereby preventing reuse of the lancet device.

In a further embodiment, a lancet device comprises a rear housing including a resiliently flexible drive structure extending therein and a forward housing engaged with and axially movable with respect to the rear housing, with the forward housing including an opening through the forward end thereof. The forward housing further includes a guide surface adapted to deflect the resiliently flexible drive structure of the rear housing during axial movement of the rear housing and the forward housing toward each other. A lancet structure including a puncturing element is maintained within an interior of the forward housing, with the lancet structure including an abutment surface for abutting engagement with the resiliently flexible drive structure of the rear housing. The resiliently flexible drive structure is adapted to drive the lancet structure axially forward to a position wherein the puncturing element extends through the opening of the forward housing upon axial movement of the rear housing and the forward housing toward each other. The device further includes a lancet retention member for retracting the puncturing element within the opening of the forward housing after it extends therethrough, upon axial movement of the rear housing and the forward housing toward each other to a position at which the guide surface deflects the resiliently flexible drive structure out of abutting engagement with the abutment surface of the lancet structure.

The resiliently flexible drive structure of the rear housing and the guide surface of the forward housing may include corresponding structure for locking engagement therebetween upon axial movement of the rear housing and the forward housing toward each other to maintain the resiliently flexible drive structure disengaged from the abutment surface of the lancet structure, thereby preventing reuse of the lancet device. For example, the guide surface of the forward housing may include a ramped surface having a notch at a forward end thereof and the resiliently flexible drive structure may include a protrusion for locking engagement between the forward housing and the rear housing.

In a further embodiment of the invention, a method of actuating a lancet device comprises providing a lancet device including a housing having a first housing portion with a drive structure and a second housing portion with a corresponding guide surface, a lancet structure including a puncturing element disposed within the housing, and a lancet retention member for maintaining the puncturing element within the housing. The method involves axially moving the first housing portion and the second housing portion with respect to each other. Such movement causes the drive structure of the first housing portion to contact an abutment surface of the lancet structure to drive the lancet structure axially through the housing to a position in which the puncturing element extends through a forward end of the housing. Such movement simultaneously guides the drive structure of the first housing portion along the guide surface of the second housing portion to deflect out of engagement with the abutment surface of the lancet structure, thereby permitting the lancet retention member to retract the puncturing element to a position retained within the housing. The lancet device may further include a lancet cover integrally molded with the lancet structure, with the method further involving a step of removing the lancet cover prior to the axially moving step.

The method may further involve a locking step, such as interengaging the drive structure of the first housing portion with a forward portion of the guide surface of the second housing portion upon deflecting of the drive structure out of engagement with the abutment surface of the lancet structure. In this manner, the drive structure is maintained disengaged from the abutment surface of the lancet structure to prevent reuse of the lancet device.

In yet a further embodiment, a lancet device includes a lancet structure comprising a puncturing element, a housing comprising a rear housing portion and a forward housing portion longitudinally movable with respect to each other, and a lancet retention member for maintaining the puncturing element within the housing. Longitudinal movement of the rear housing portion with respect to the forward housing portion causes the lancet structure to move substantially in conjunction with the rear housing portion, thereby causing exposure of the puncturing element through the forward housing portion. The lancet retention member retracts the puncturing element within the forward housing portion. The rear housing portion further includes a locking structure for locking engagement with the forward housing portion as a result of the longitudinal movement, thereby preventing re-exposure of the puncturing element through the forward housing portion.

Desirably, the rear housing portion frictionally engages the forward housing portion thereby causing frictional interference between the rear housing portion and the forward housing portion. As such, exposure of the puncturing element is caused when the frictional interference is overcome by a force for enabling the longitudinal movement. Moreover, the rear housing portion may further comprise structure for abutting engagement with the lancet structure. As such, longitudinal movement causes the lancet structure to move substantially in conjunction with the rear housing portion based on such abutting engagement. In such an embodiment, the forward housing portion may include a guiding surface adapted for engagement with the abutting engagement structure of the rear housing portion. The longitudinal movement can therefore cause the abutting engagement structure to engage the guiding surface, thereby disengaging the structure from abutting engagement with the lancet structure during exposure of the puncturing element. For example, the abutting engagement structure of the rear housing portion may comprise at least one resiliently deflectable finger extending from the rear housing portion, with the guiding surface of the forward housing portion comprising at least one corresponding ramped surface. In this manner, the at least one resiliently deflectable finger can slide along the at least one corresponding ramped surface to deflect radially outwardly upon longitudinal movement of the housing portions with respect to each other.

Further, the guide surface of the forward housing portion may comprise a ramped surface having a notch for interference engagement with a protrusion of the abutting engagement structure of the rear housing portion upon longitudinal movement of the housing portions. Such interference engagement can establish a locking structure, thereby preventing reuse of the lancet device.

In a further embodiment, a lancet device comprises a lancet structure comprising a puncturing element, and a housing comprising a first housing portion and a second housing portion axially movable with respect to each other. The first housing portion includes structure for abutting engagement with a corresponding surface of the lancet structure, and the second housing portion includes a guiding surface adapted for engagement with the abutting structure of the first housing portion during axial movement of the first housing portion and the second housing portion with respect to each other. A lancet retention member is also provided for maintaining the puncturing element of the lancet structure within the housing. Axial movement of the first housing portion with respect to the second housing portion causes the abutting structure of the first housing portion to move the lancet structure to a position wherein the puncturing element extends through a forward end of the second housing portion due to the abutting engagement between the abutting structure and the lancet structure. Such axial movement also causes the abutting structure to engage the guiding surface of the second housing portion to disengage the abutting structure from the abutment surface upon extension of the puncturing element through the forward end of the second housing portion, thereby permitting the lancet retention member to retract the puncturing element within the forward end of the second housing portion.

Desirably, the first housing portion frictionally engages the second housing portion thereby causing frictional interference between the first housing portion and the second housing portion. Such frictional interference prevents axial movement of the first housing portion with respect to the second housing portion until the frictional interference is overcome by a pre-determined force value. In particular embodiments, the pre-determined force value exceeds a minimum force value which is required to cause axial movement of the first housing portion with respect to the second housing portion, which thereby causes the puncturing element to extend through a forward end of the second housing portion and causes the abutting structure to engage the guiding surface of the second housing portion to disengage the abutting structure from the abutment surface upon extension of the puncturing element through the forward end of the second housing portion, thereby permitting the lancet retention member to retract the puncturing element within the forward end of the second housing portion.

In still a further embodiment, a method is provided for actuating a lancet device. The method involves providing a lancet device comprising a housing having a first housing portion and a second housing portion in frictional interference with respect to each other, a lancet structure including a puncturing element disposed within the housing, and a lancet retention member for maintaining the puncturing element within the housing. In the method, pressure is applied between the first housing portion and the second housing portion at a force sufficient to overcome the frictional interference between the first housing portion and the second housing portion. As such, the first housing portion and the second housing portion are caused to move longitudinally with respect to each other such that an abutting surface of the first housing portion moves the lancet structure substantially in conjunction with the first housing portion to cause the puncturing element to extend through a forward end of the second housing portion. Also, the abutting surface is caused to disengage from the lancet structure, thereby permitting the lancet retention member to retract the puncturing element to a position retained within the housing after extending through a forward end of the second housing portion. A locking step may further be provided, which comprises interengaging the first housing portion with the second housing portion upon disengagement of the abutting surface from the lancet structure, thereby preventing reuse of the lancet device.

Desirably, the second housing portion comprises a guide surface such that said longitudinal movement causes the abutting surface to guide along the guide surface to deflect out of engagement with the lancet structure, thereby permitting the lancet retention member to retract the puncturing element to a position retained within the housing after extending through a forward end of the housing. In particular embodiments, the force required to overcome the frictional interference between the first housing portion and the second housing portion is greater than the force required to cause the first housing portion and the second housing portion to move longitudinally with respect to each other. As such, the puncturing element is automatically caused to extend through a forward end of the second housing portion when the frictional interference is overcome, thereby causing the abutting surface to disengage from the lancet structure, and causing the lancet retention member to retract the puncturing element to a position retained within the housing after extending through a forward end of the second housing portion.

Further details and advantages of the invention will become apparent from the following detailed description when read in conjunction with the accompanying drawings.

BRIEF DESCRIPTION OF THE DRAWINGS

FIG. 5A and FIG. 5B are rear and front perspective views, respectively, of a forward housing in an embodiment of the lancet device of the present invention.

DESCRIPTION OF THE PREFERRED EMBODIMENTS

Figure 1:
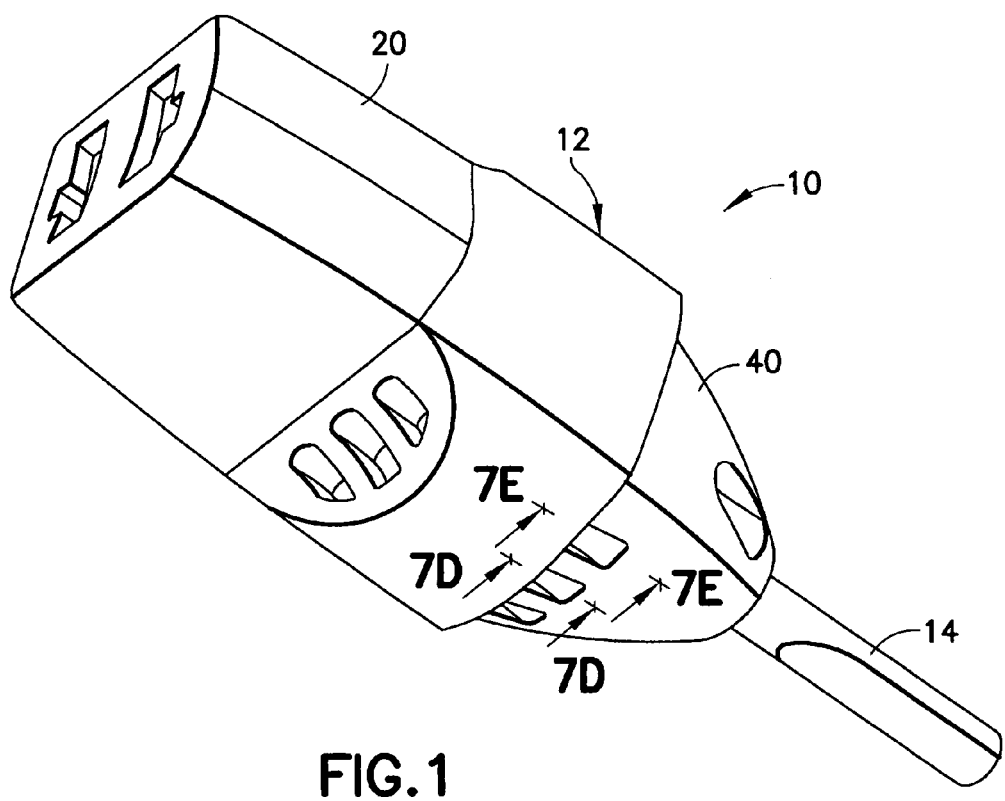
FIG. 1 is perspective view of a lancet device in accordance with an embodiment of the present invention.

For purposes of the description hereinafter, the words "upper", "lower", "right", "left", "vertical", "horizontal", "top", "bottom", "lateral", "longitudinal" and like terms, if used, shall relate to the described embodiments as oriented in the drawing figures. However, it is to be understood that many alternative variations and embodiments may be assumed except where expressly specified to the contrary. It is also to be understood that the specific devices and embodiments illustrated in the accompanying drawings and described herein are simply exemplary embodiments of the invention.

Figure 2:
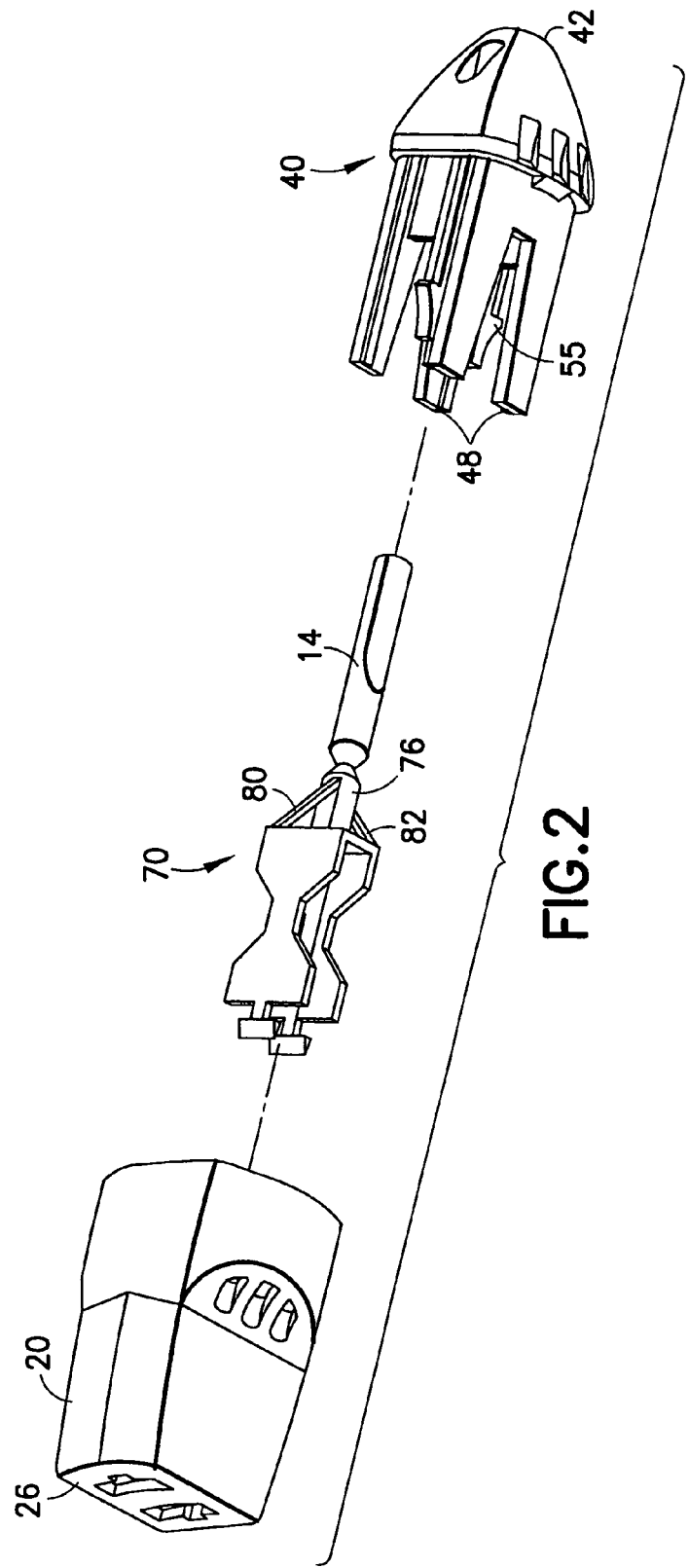
FIG. 2 is an exploded perspective view of the lancet device of FIG. 1.
Figure 3:
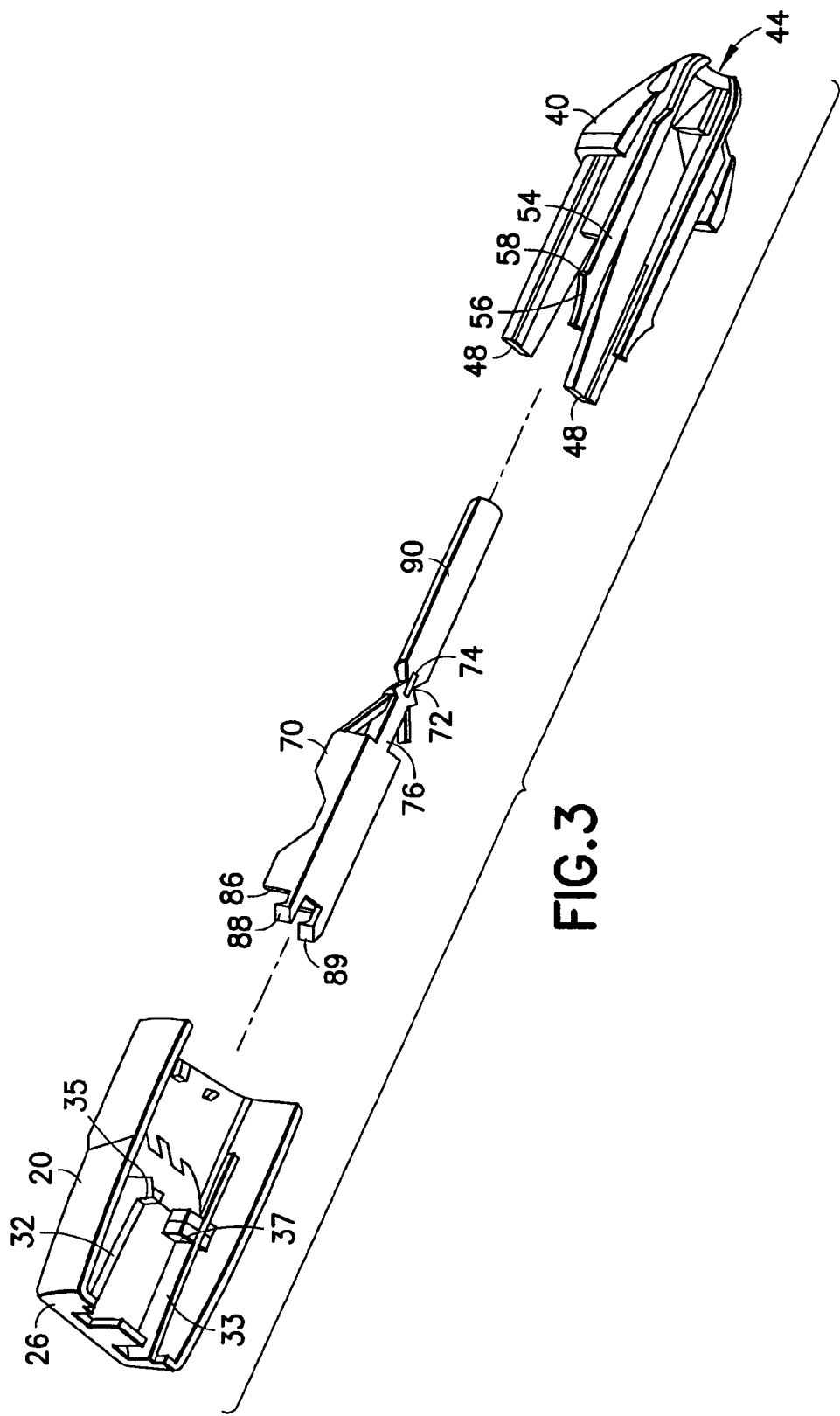
FIG. 3 is an exploded perspective sectional view of the lancet device of FIG. 1.

Referring to FIGS. 1-3, a lancet device 10 according to an embodiment of the invention is generally shown. The lancet device 10 generally includes a main housing 12 including a proximal or rear housing body 20 and a distal or forward housing body 40 movably associated therewith, and a lancet structure 70 disposed therein. As will be discussed in greater detail herein, the forward housing body 40 is coaxially and movably associated with the rear housing body 20, with the lancet structure 70 contained within and axially movable therethrough. A protective cover 14 is further provided to ensure sterility of the lancet prior to use.

The main housing 12 defines an elongated body, and is desirably formed with a first housing portion defining a proximal or rearward end portion and a second housing portion defining a distal or forward end portion, such as rear housing body 20 and a forward housing body 40, respectively. In this manner, the main housing 12 is formed of separate structures which may be interfitted together and attached to each other, such as through a mechanical engagement, permitting axial movement toward each other while preventing or resisting detachment after being assembled together. For purposes of the present invention, the rear housing body 20 and the forward housing body 40 are described herein in terms of axial movement with respect to each other. It is to be understood that such axial movement contemplates any movement of the rear housing body 20 and the forward housing body 40 relative to each other, including longitudinal movement of either body or both bodies with respect to the general length of the main housing assembly. It is also contemplated that certain embodiments of the invention may include a non-linear axis for the main housing assembly defined by rear housing body 20 and forward housing body 40. The terms axial and longitudinal are used interchangeably through the present application to describe relative movement of the housing bodies with respect to each other, and such terms are intended to encompass all such embodiments or relative movement.

The interior portion of the main housing 12 is generally open defining an internal cavity which is generally closed at the rearward end through rear housing body 20 and at the forward end through forward housing body 40, with an opening 44 through a forward end of the forward housing body 40 through which the puncturing end 74 of the lancet structure can extend, as will be discussed in further detail herein.

Figure 4A:
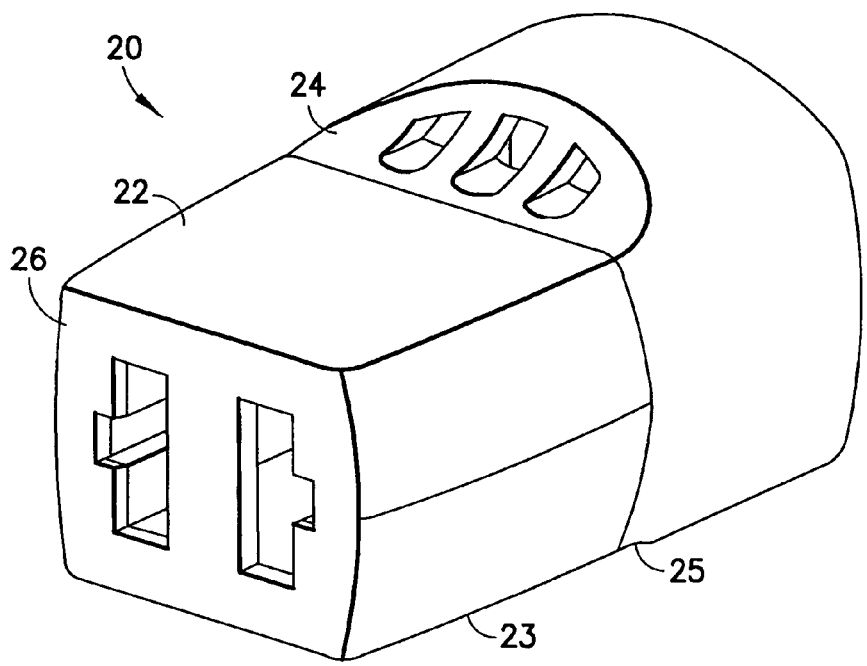
FIGS. 4A-4B are perspective views of a rear housing in an embodiment of the lancet device of the present invention.
Figure 4B:
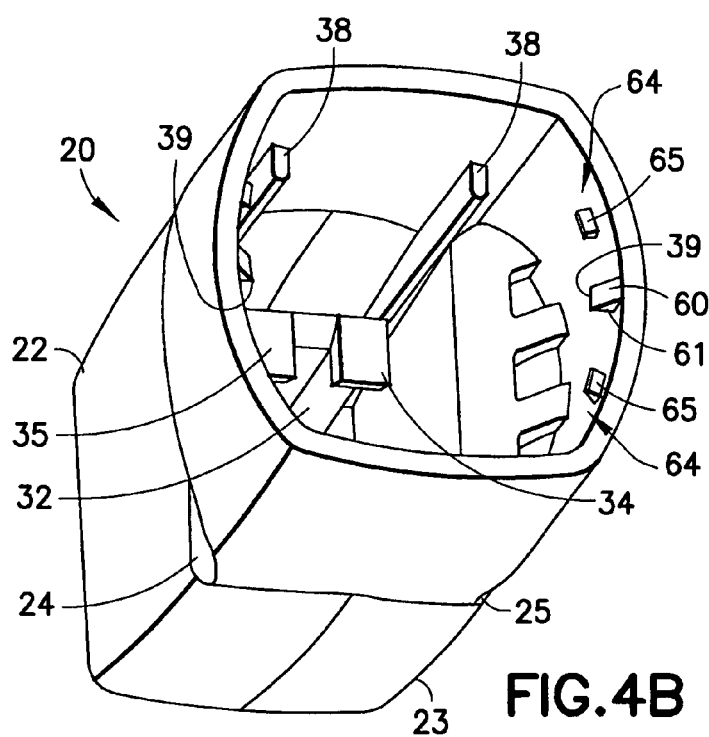

As depicted in FIGS. 4A-4B, rear housing body 20 is somewhat elongated in shape defining opposed sides 22, 23, which may each include a surface for accommodating a user's fingers, such as finger grip indentations 24, 25. While two opposed finger grip indentations 24, 25 are shown on the rear housing body 20, it will be appreciated that only one finger grip indentation 24 formed in the rear housing body 20 may be provided. The finger grip indentations may be formed in any profile for accommodating a user's finger, such as concave depressions, recesses, or sloped surfaces on the outer surface of the rear housing body 20. Additionally, the rearward end 26 of rear housing body 20 may also include a surface for accommodating a user's finger, which may also be formed as a concave depression or recess. The side finger grip indentations 24, 25 and the rearward end 26 provide ergonomically shaped surfaces that substantially conform to a user's fingertips to aid the user in manipulating the lancet device 10 and using the lancet device 10 in a blood letting, drawing, or collection procedure, and may provide multiple finger grip positions for the user.

Figure 5C:
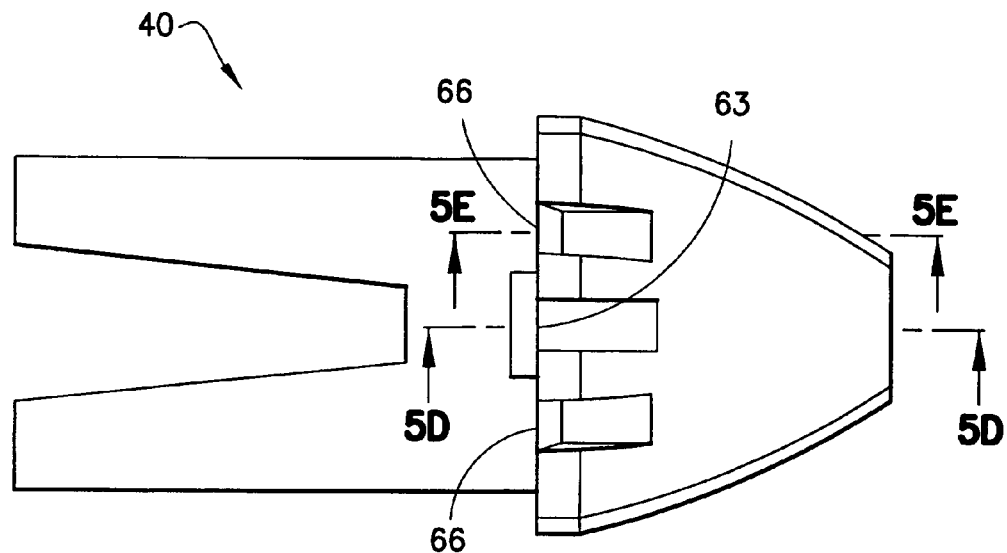
FIG. 5C is side view of the forward housing shown in FIGS. 5A and 5B.
Figure 5D:
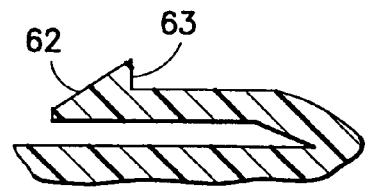
FIG. 5D is a sectional view taken along line 5D-5D of FIG. 5C.
Figure 5E:
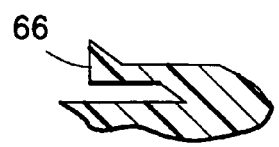
FIG. 5E is a sectional view taken along line 5E-5E of FIG. 5C.

Main housing 12 further includes forward housing body 40 which extends outward from the forward end of the rear housing body 20. As shown in FIGS. 5A-5B, the forward housing body 40 is a generally hollow structure defining a forward end 42, having opening 44 therethrough, through which the puncturing element extends when the lancet device 10 is actuated by the user, as will be discussed in more detail herein. Forward housing body 40 may include structure for engagement with rear housing body 20, such as a frame 46 extending rearwardly for interfitting within the internal cavity of rear housing body 20. Forward housing body 40 may include a profile which narrows or generally tapers toward the forward end 42 to define a small contact area about the distal opening 44 for contacting the intended area on the user's body which is to be punctured by the puncturing element.

The rear housing body 20 and the forward housing body 40 are designed to be axially or longitudinally movable with respect to each other, i.e., toward each other. The force required to move rear housing body 20 and forward housing body 40 with respect to each other varies depending upon the relative positioning of the forward housing body 40 with respect to the rear housing body 20. The rear housing body 20 and the forward housing body 40 may therefore include corresponding guiding surfaces for guiding the forward housing body 40 axially through the rear housing body 20. For example, frame 46 of the forward housing body 40 may comprise a plurality of legs 48, which may engage and interact with corresponding rails 38 extending along the interior surface of rear housing body 20. Such corresponding surfaces ensure that the forward housing body 40 is properly aligned within rear housing body 20, and further provide for sliding axial movement of the forward housing body 40 within the rear housing body 20, desirably preventing or resisting rotational movement. Additionally, rear housing body 20 and forward housing body 40 may include corresponding structure for abutting or interference engagement therebetween, to prevent forward housing body 40 from axially sliding completely out of rear housing body 20. Such engagement establishes a maximum axial or longitudinal extension position of rear housing body 20 and forward housing body 40 with respect to each other, in which the forward housing body 40 is prevented from sliding away from rear housing body 20 after being assembled therewith. For example, rear housing body 20 may include one or more clips 39 for interfitting or interfering engagement with one or more corresponding clips 50 of forward housing body 40, thereby locking forward housing body 40 within rear housing body 20.

Rear housing body 20 and forward housing body 40 may also include additional corresponding structure for interference engagement therebetween, which provides for an override or threshold engagement for relative movement therebetween. Such an override or threshold interfering engagement may be in addition to the interfitting engagement establishing the maximum extension position of rear housing body 20 with respect to forward housing body 40, as noted above. This override or threshold interfering engagement provides a mechanism for assuring that a pre-determined amount of frictional interference is overcome prior to movement of rear housing body 20 and forward housing body 40 with respect to each other. As will be discussed in more detail herein with respect to use of lancet device 10, such frictional interference established through this threshold interfering engagement requires a sufficient amount of force to build up from the applied pressure such that once the frictional interference is overcome, sufficient force will continue to be transferred to the device to cause puncturing of the patient's skin. For example, as shown in FIG. 4B, rear housing body 20 may include abutment structures 64 adjacent to clip 39 at opposing sides thereof, with surface edges 65 at a forward edge thereof. As shown in FIGS. 5B-5E, forward housing body 40 may include corresponding face edges 66 adjacent clip 50 at opposing sides thereof. When clips 39 and clips 50 are interfitted together, surface edges 65 of abutment structures 64 on rear housing body 20 are in interference or abutting engagement with corresponding face edges 66 of forward housing body 40. Such interference engagement provides a mechanism which prevents rear housing body 20 and forward housing body 40 from being accidentally moved toward each other, since a sufficient amount of pressure must be applied therebetween to overcome the pre-determined threshold of pressure, and thereby overcome the interference engagement between surface edges 65 and face edges 66. Also, such interference engagement provides a mechanism by which the amount of pressure required to cause rear housing body 20 to move with respect to forward housing body 40 is sufficient to cause complete actuation of lancet device 10, resulting in puncturing of the patient's skin and safe retraction of the lancet, as will be discussed in greater detail herein.

Figure 6:
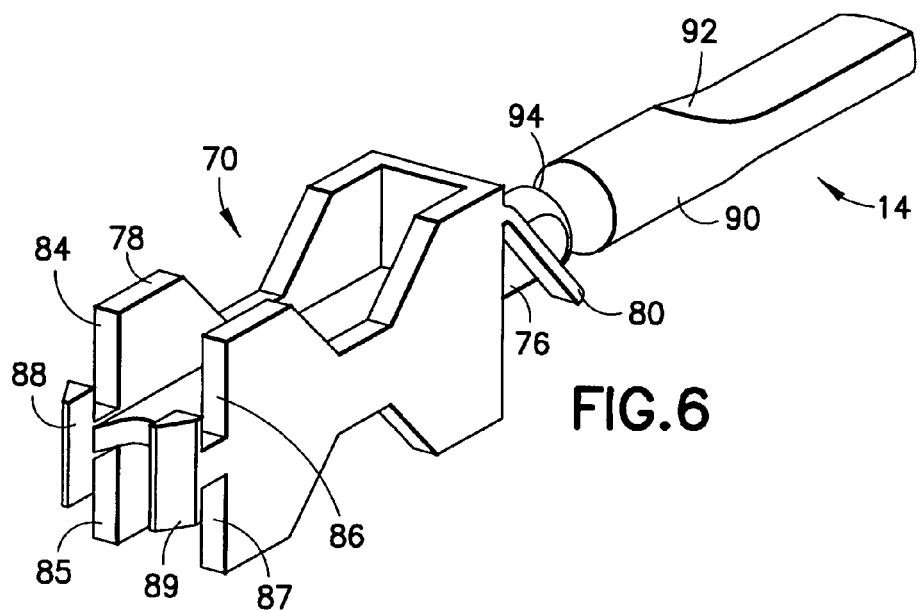
FIG. 6 is a perspective view of a lancet structure in an embodiment of the lancet device of the present invention.
Figure 7B:
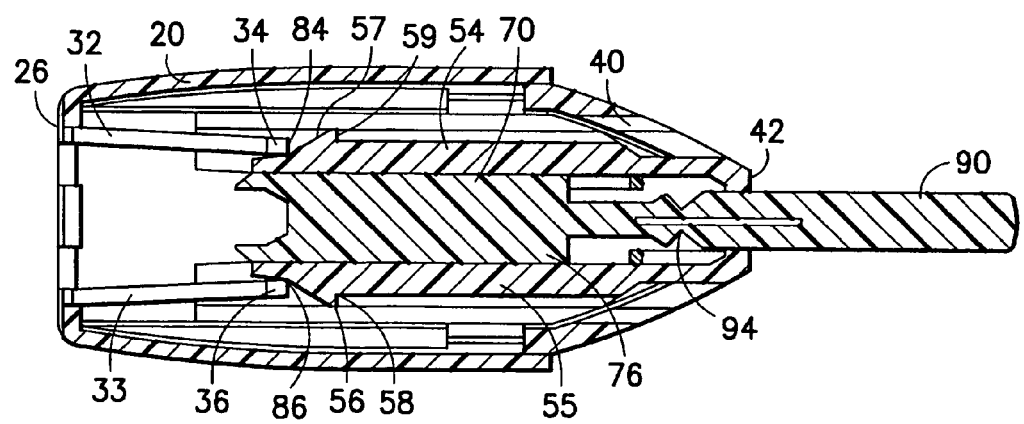
FIG. 7B is a cross-sectional view of the lancet device of FIG. 1.

Lancet device 10 further includes a lancet structure 70 disposed within the main housing 12. As shown in FIGS. 6-7B, lancet structure 70 includes a puncturing element, shown in the form of lancet 72 defining a puncturing end 74 at the forward end thereof. Lancet structure 70 is adapted for axial movement through the main housing 12 between an initial position with the puncturing end 74 maintained within the forward end of forward housing body 40 to a puncturing position in which the puncturing end 74 extends beyond the forward opening 44 of forward housing body 40, as will be discussed further herein in terms of use of the lancet device 10. Puncturing end 74 is adapted for puncturing the skin of a patient, and may define a pointed end, a blade edge, and the like. Puncturing end 74 may also include a preferred alignment orientation, such as with a pointed end of a blade aligned in a specific orientation.

Lancet structure 70 further includes a carrier element 76 supporting lancet 72 at the rearward end thereof. The carrier element 76 and forward housing body 40 may include corresponding guiding surfaces for guiding the lancet structure 70 therethrough. For example, carrier element 76 may include guide tabs 78 on an external surface thereof, with the forward housing body 40 including corresponding guide channels 52 extending longitudinally along an inner surface thereof for accommodating guide tabs 78 slidably therein. It is contemplated that other guiding surfaces may also be used. The guide tabs 78 and guide channels 52 ensure that the lancet structure 70 is properly aligned within forward housing body 40, and provide for sliding axial movement of the lancet structure 70 within the forward housing body 40, while preventing or resisting rotational movement about, for example, the longitudinal axis of lancet device 10.

Lancet device 10 further includes a lancet retention member for maintaining the puncturing end 74 of lancet structure 70 within the main housing 12, particularly after normal use thereof. For example, lancet device 10 may include specific structure which is provided to maintain the puncturing end 74 within the housing, such as a structure biasing the lancet structure 70 internally away from the forward end of the forward housing body 40 to a position wherein the puncturing end 74 of the lancet structure 70 is maintained within the internal portion of forward housing body 40. For example, one or more leaf springs 80, 82 may be provided between the forward end of lancet structure 70 and the inner surface within the forward end 42 of the forward housing body 40. In one embodiment, such leaf springs 80, 82 may be integrally molded with a portion of lancet device 10, such as with the forward housing body 40, or with the lancet structure 70, as shown in FIG. 6. In this manner, the leaf springs 80, 82 are adapted for maintaining the lancet structure 70 within the housing 12 and for retracting the lancet structure 70 within the forward housing body 40 after the lancet structure 70 is axially moved to the puncturing position. It is contemplated that any mechanism adapted for retaining the lancet structure 70 within the housing 12 may be used in the invention, such as a compression type spring positioned between the lancet structure 70 and the forward end of the forward housing body 40, which may be attached to either the lanced structure, the forward housing body or both, or optionally an extension spring positioned between the rear housing body 20 and the lancet structure 70, and attached to either the lancet structure, the forward housing body, or both, for example.

Figure 7A:
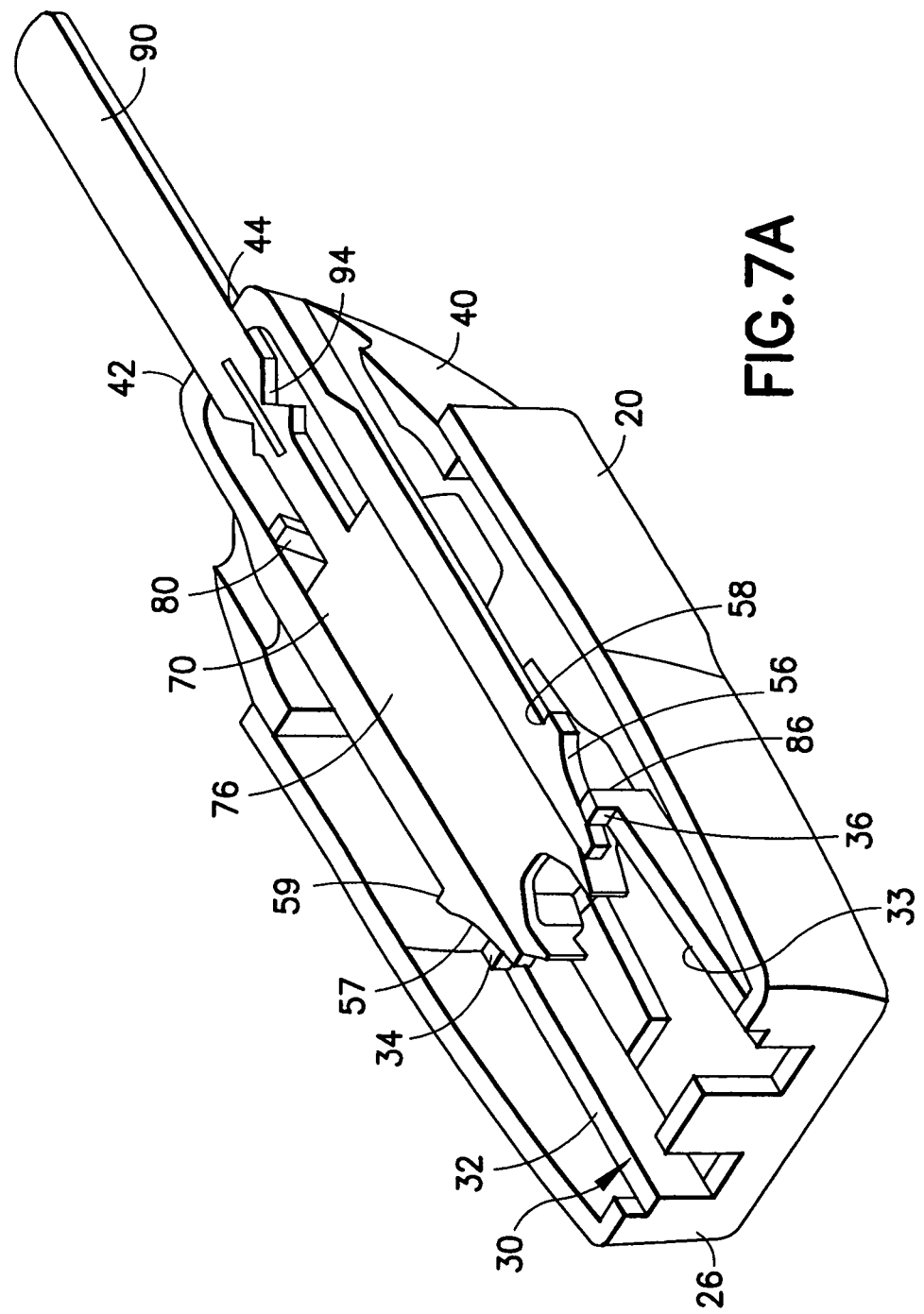
FIG. 7A is a perspective sectional view of the lancet device of FIG. 1.

With lancet retention member such as leaf springs 80, 82 maintaining the puncturing end 74 of lancet structure 70 within the main housing 12, lancet device 10 further includes a mechanism for causing the puncturing element at puncturing end 74 of lancet 72 to extend through the opening 44 at forward end 42 of forward housing body 40. In particular, as depicted in FIGS. 3 and 7A-7B, rear housing body 20 may include drive structure 30 for effecting movement of the lancet structure 70 with respect to the forward housing body 40. Drive structure 30 provides a mechanism for causing movement of the lancet structure 70 with respect to forward housing body 40 to the puncturing position against any retaining force of the lancet retention member holding the lancet within housing 12. Such force or driving movement is provided through an interference or abutting engagement between the drive structure 30 and the lancet structure 70. As will be discussed in further detail herein, the force or momentum for driving the lancet structure 70 with respect to the forward housing body 40 is directly provided through the force of the user applying pressure to the lancet device 10 against the skin. In this manner, the lancet device 10 of the present invention can be considered an "inertia-powered" device, in that the driving momentum forcing the lancet to the puncturing position for puncturing the skin is accomplished directly through the force of the user, as opposed to the user activating a separate structure which is triggerable, such as a compression-type drive spring which can be compressed and released to provide the driving force for movement of the lancet, as is commonly used in the art. Such an "inertia-powered" effect is particularly apparent in embodiments of the invention in which a frictional interference engagement is provided between the rear housing body 20 and the forward housing body 40 which provides for an override or threshold engagement therebetween, with a pre-determined threshold level of pressure required to be applied or exerted between the rear housing body 20 and the forward housing body 40 which will automatically cause puncturing of the skin upon reaching the threshold level of pressure required to release the interference engagement therebetween.

Since the drive structure 30 provides the force or driving movement through an interference or abutting engagement with the lancet structure 70, the drive structure 30 must be sufficiently resilient or stiff so as to exert and maintain a driving force upon lancet structure 70 when pressure is applied to the rear housing body 20 with lancet device 10 held against a patient's skin. In an embodiment as depicted in the figures, drive structure 30 may include one or more resiliently flexible fingers 32, 33 which extend within the interior of rear housing body 20. As shown in FIG. 3, such fingers 32, 33 may extend from the rearward wall of rear housing body 20 toward the forward end of lancet device 10. In one embodiment, fingers 32, 33 are integrally molded with the rear housing body 20, providing an integral structure.

As noted, drive structure 30 is adapted to interferingly or abuttingly engage with the lancet structure 70 so as to provide a mechanism for driving lancet structure 70. This engagement may be accomplished by providing interfering structures or abutting surfaces on corresponding surfaces of drive structure 30 and lancet structure 70. For example, fingers 32, 33 may each include one or more protrusions 34, 35 and 36, 37, respectively. Also, lancet structure 70 may include abutment surfaces 84, 85 and 86, 87 on a rearward end thereof, for abutting relation with protrusions 34, 35 and 36, 37 of fingers 32, 33. In this manner, the forward edge surfaces of each of the protrusions 34, 35 and 36, 37, abut and press against the abutment surfaces 84, 85 and 86, 87 of the lancet structure 70, thereby driving the lancet structure 70 during use, as will be discussed in more detail.

Figure 7C:
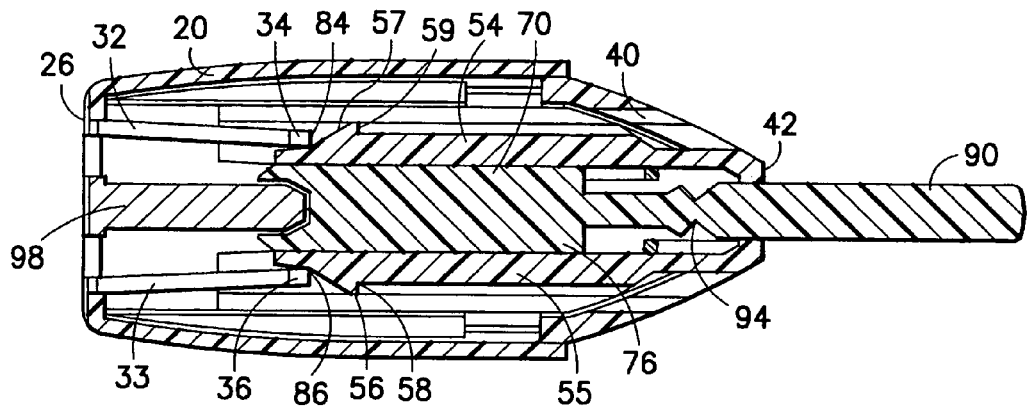
FIG. 7C is a cross-sectional view of a lancet device in an alternate embodiment, showing a further drive post for contact with the lancet structure.

It is further contemplated that additional structure may be present within lancet device 10 to assist in the movement of lancet structure 70 through the forward housing body 40 to achieve the puncturing position. For example, as shown in FIG. 7C, a drive post 98 may further be provided extending from an internal surface of the rearward end of rear housing body 20. Drive post 98 is provided for contact with the rear end of carrier element 76 of lancet structure 70 during use. In this manner, as rear housing body 20 is moved axially or longitudinally with respect to forward housing body 40, drive post 98 contacts the rear end of lancet structure 70, thereby causing lancet structure 70 to move through forward housing body 40 toward the puncturing position.

Drive structure 30 and lancet structure 70 may further include structure to prevent disengagement after assembly. For example, finger 32 may include a gap between protrusions 34, 35, and finger 33 may include a similar gap between protrusions 36, 37. Lancet structure 70 may include one or more clips, such as clips 88, 89 shown in FIGS. 3 and 6, extending rearwardly therefrom for locking engagement with the corresponding gaps extending between protrusions 34, 35 and 36, 37 on each of fingers 32, 33. In this manner, an interlocking structure can be established between clips 88, 89 and the gap between the protrusions 34, 35 and 36, 37 of fingers 32, 33, thereby lockingly engaging the lancet structure 70 to the drive structure 30.

As noted, the lancet structure 70 is further adapted to retract within housing 12 after the puncturing element achieves the puncturing position. This is accomplished by providing a mechanism to release the interference engagement between the drive structure 30 and the lancet structure 70 during the driving momentum. For example, as discussed above, fingers 32, 33 are sufficiently resilient or stiff so as to drive lancet structure 70 forward through housing 12 and through the skin surface based directly on a driving pressure applied thereto, without collapsing or bending out of interference engagement. Fingers 32, 33 are also sufficiently flexible or deflectable so as to disengage from the interference engagement with abutment surfaces 84, 85 and 86, 87, when the puncturing position is achieved, such as by deflecting out of engagement. In particular, fingers 32, 33 are sufficiently flexible so as to deflect away from the abutment surfaces 84, 85 and 86, 87, such as by deflecting radially outwardly with respect to the general axis of lancet device 10, thereby releasing any interference engagement established between the forward edge surfaces of each of the protrusions 34, 35 and 36, 37, pressing against the abutment surfaces 84, 85 and 86, 87. This radial deflection may be accomplished by providing additional structure within lancet device 10 for interfering with fingers 32, 33 during axial movement between the rear housing body 20 and the forward housing body 40. For example, forward housing body 40 may include structure extending toward a rearward end thereof, such as one or more extensions 54, 55. Such extensions 54, 55 may include a profile for deflecting fingers 32, 33, such as sloped or ramped surfaces 56, 57, which permit sliding or gliding movement of fingers 32, 33 thereover during axial movement of rear housing body 20 and forward housing body 40 toward each other. Such sliding movement guides fingers 32, 33 out of engagement from the abutment surfaces 84, 85 and 86, 87 of lancet structure 70, as will be discussed in further detail herein with respect to use of the device. Extensions 54, 55 may further include notches 58, 59 at a forward end of ramped surfaces 56, 57, providing a locking mechanism for interference engagement with fingers 32, 33 after deflection thereof.

Lancet device 10 may further include a protective cover 14 for protectively covering the puncturing end 74 of the lancet structure 70 prior to use thereof in order to maintain sterility. The protective cover 14 defines a cover body 90 which may extend within the opening 44 of the forward housing body 40 to encompass at least a portion of the puncturing element, thereby protectively surrounding and encompassing at least a portion of the puncturing element, namely lancet 72. A tab member 92 may extend from the cover body 90 beyond the opening 44 of the forward housing body. Referring generally to FIG. 6, cover body 90 is desirably formed integrally with carrier element 76 of lancet structure 70, completely encompassing lancet 72, thereby maintaining sterility thereof prior to use. Cover body 90 and carrier element 76 may include a notched portion 94 at a juncture therebetween, providing a fraction point for cover body 90 and exposing lancet 72. Alternatively, the cover body 90 may be secured directly to the lancet 72 by methods customary in the medical field, such as with a releasable medical grade adhesive.

Figure 7D:
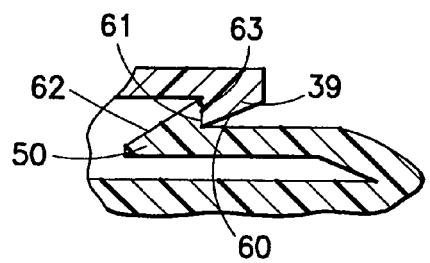
FIG. 7D is a cross-sectional view of a portion of an assembled lancet device corresponding to the portion shown at lines 7D-7D of FIG. 1, showing the engagement between the clips of the rear and forward housing bodies, with the lancet device in a state ready for use.
Figure 7E:
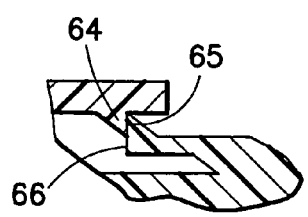
FIG. 7E is a cross-sectional view of a portion of an assembled lancet device corresponding to the portion shown at lines 7E-7E of FIG. 1, showing the abutting engagement between the corresponding edge surfaces within the rear and forward housing bodies, with the lancet device in a state ready for use.

The respective elements of the lancet device are all typically formed of molded plastic material, such as a medical grade plastic material. The lancet 72 may be constructed of any suitable material adapted for puncturing the skin, and is typically a surgical grade metal such as stainless steel. Desirably, the lancet device is assembled from three separate structures as depicted in FIG. 3. For example, the lancet structure 70 is desirably provided as an insert molded structure with the lancet 72 insert molded within the lancet structure 70, including the lancet carrier 76, leaf springs 80, 82, the cover body 90 and tab member 92 integrally molded thereover. Lancet structure 70 can then be inserted within the forward housing body 40 such that tab 92 of cover body 90 extends through the opening 44. Rear housing body 20 can then be attached over forward housing body 40 with legs 48 of frame 46 aligned with rails 38 within rear housing body 20. Clips 88, 89 of lancet structure 70 snap fit with fingers 32, 33 at the gaps between the protrusions 34, 35 and 36, 37, respectively. Further, as rear housing body 20 is aligned with forward housing body 40, ramped surface 60 of clips 39 of rear housing body 20 ride along corresponding ramped surfaces 62 of clips 50 of forward housing body 40, until a point at which clips 39 snap-fit with clips 50. In this manner, clip shoulder 61 of clip 39 is in an interference engagement with clip shoulder 63 of clip 50, thereby assembling rear housing body 20 and forward housing body 40 as housing 12, and forming lancet device 10 including lancet structure 70 contained within housing 12. Movement of forward housing body 40 within rear housing body 20 is momentarily prevented due to the interference engagement established through face edges 66 of forward housing body 40 abutting against the surface edges 65 of abutments 64 of rear housing body 20, as shown in FIGS. 7D-7E. In this manner, activation of lancet device 10 will not be achieved until the user applies sufficient pressure to cause activation, thereby preventing accidental activation.

Use of the lancet device 10 will now be described with general reference to FIGS. 1-18, and particular reference to FIGS. 7A-10B. Prior to use, lancet device 10 is provided as shown in FIGS. 1 and 7A-7B, with protective cover 14 covering lancet 72. Lancet device 10, and in particular lancet structure 70, is in an initial pre-activation state, with leaf springs 80, 82 exerting a biasing force between the lancet structure 70 and the inside forward wall of forward housing body 40, thereby maintaining puncturing end 74 of lancet structure 70 within housing 12.

Figure 8A:
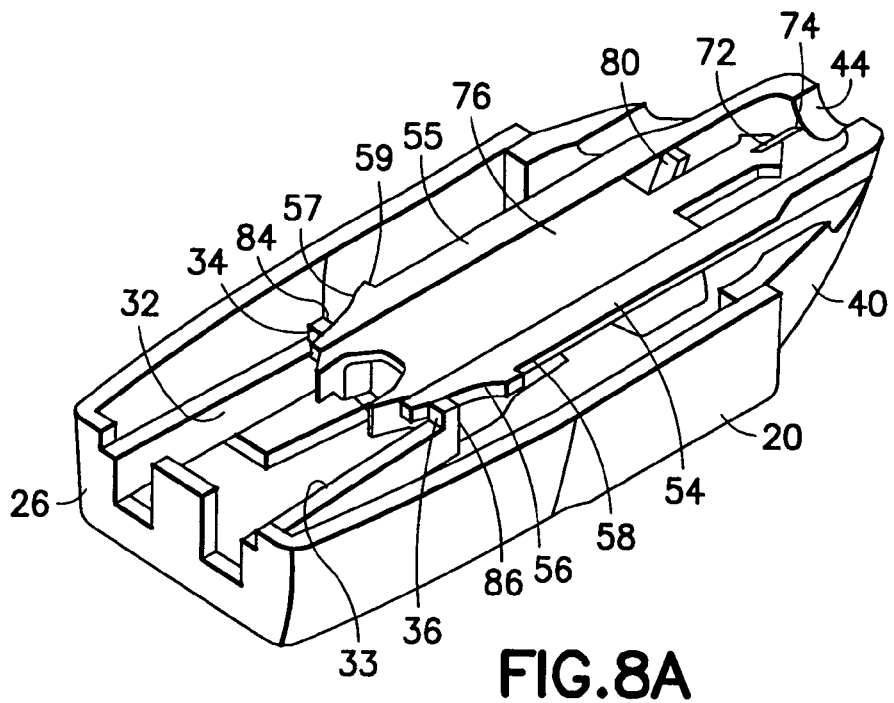
FIG. 8A is a perspective sectional view of the lancet device of FIG. 1 with the tab member removed and ready for use.
Figure 8B:
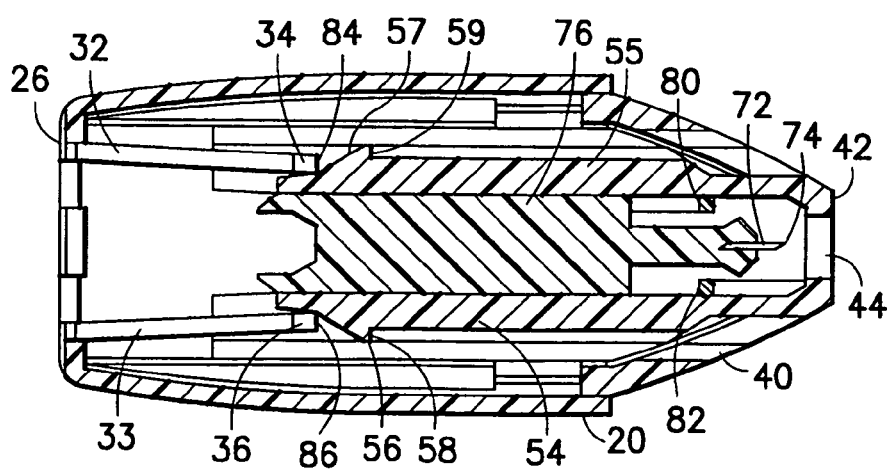
FIG. 8B is a cross-sectional view of the lancet device of FIG. 1 with the tab member removed and ready for use.

To prepare the lancet assembly for use, the user grasps housing 12, such as between a finger and thumb on opposing sides 22, 23, and removes the protective cover 14 from the forward end as shown in FIGS. 8A-8B, thereby exposing the puncturing end 74 of lancet 72 within housing 12. The tab member 92 may be ergonomically formed to allow the user to easily manipulate the tab member 92 and apply the necessary force to break the cover body 90 from the carrier element 76 at the notch 94 to thereby release the cover body 90 from the lancet 72. The applied breaking force is in accordance with the present invention and may be a singular twisting or pulling motion, or a combined "twisting" (i.e. rotational) and "pulling" motion applied for breaking the connection between the cover body 90 and the carrier element 76. The locking engagement of clips 88, 89 of lancet structure 70 with fingers 32, 33 of rear housing body 20 prevent any activation of the lancet device 10 during removal of the protective cover 14 in this manner.

The forward end 42 of forward housing body 40 may then be contacted with a location on the skin surface of a user's body or another person's body where it is desired to initiate blood flow. If provided, target indicia on the lancet device 10 may be aligned with the desired location of puncture.

Figure 9A:
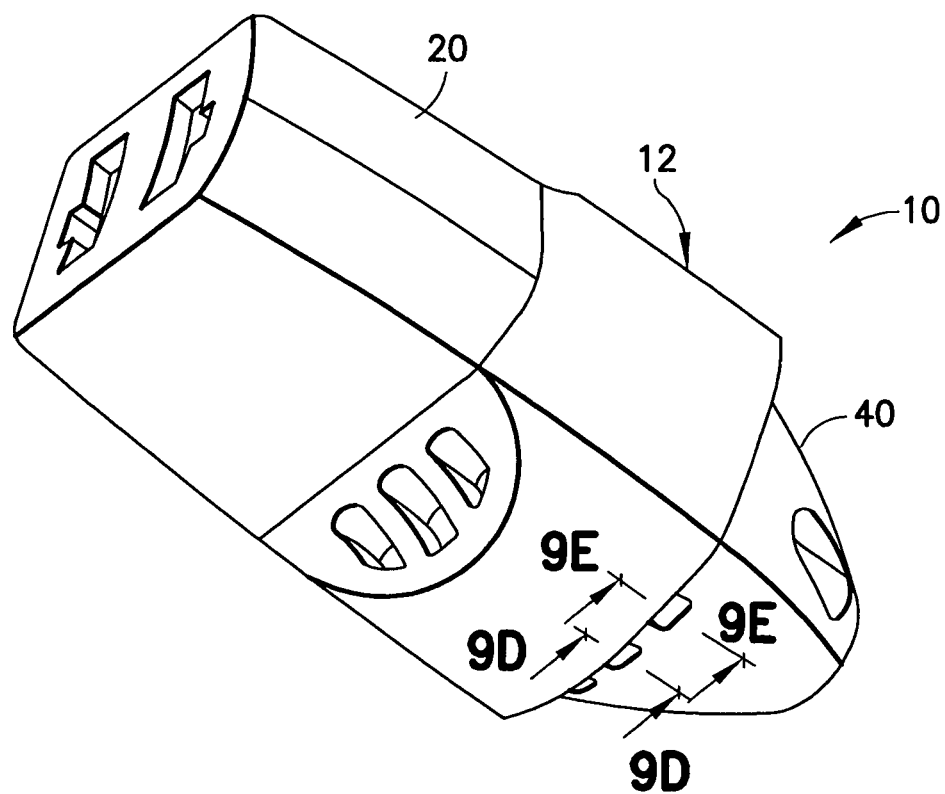
FIG. 9A is a perspective view of the lancet device of FIG. 1 in use.
Figure 9B:
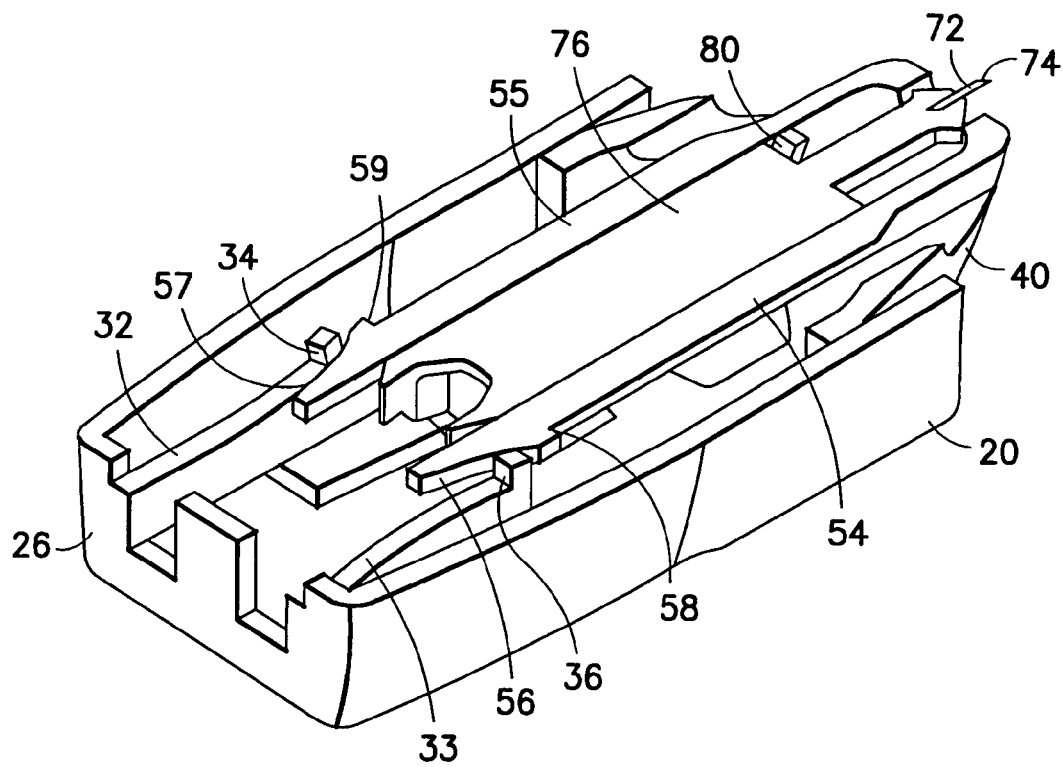
FIG. 9B is a perspective sectional view of the lancet device of FIG. 1 in use with the lancet structure in the puncturing position.
Figure 9C:
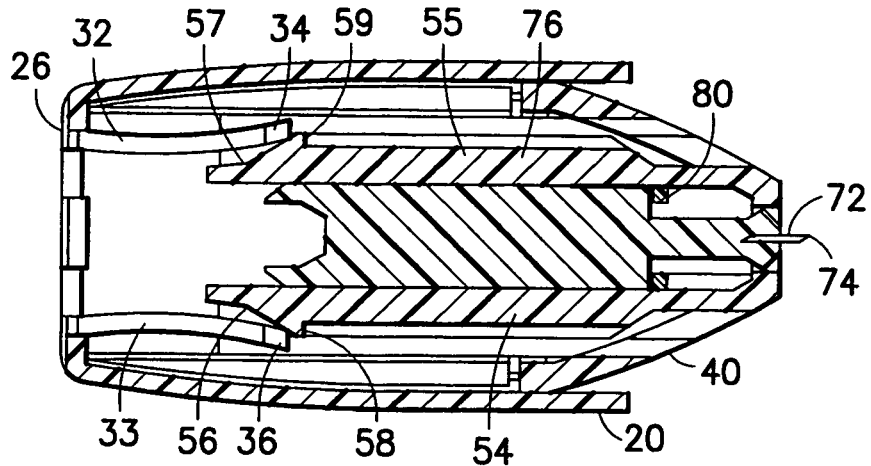
FIG. 9C is a cross-sectional view of the lancet device of FIG. 1 in use with the lancet structure in the puncturing position.
Figure 9D:
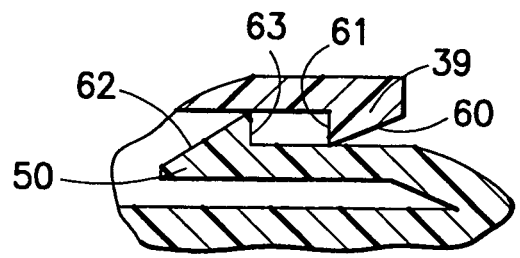
FIG. 9D is a cross-sectional view of a portion of an assembled lancet device corresponding to the portion shown at lines 9D-9D of FIG. 9A, showing the clips of the rear and forward housing bodies after the threshold force has been surpassed.
Figure 9E:
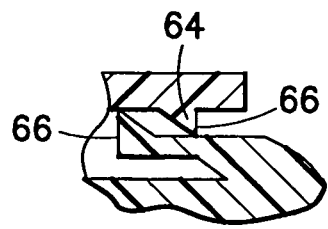
FIG. 9E is a cross-sectional view of a portion of an assembled lancet device corresponding to the portion shown at lines 9E-9E of FIG. 9A, showing the corresponding edge surfaces within the rear and forward housing bodies after the threshold force has been surpassed.
Figure 10A:
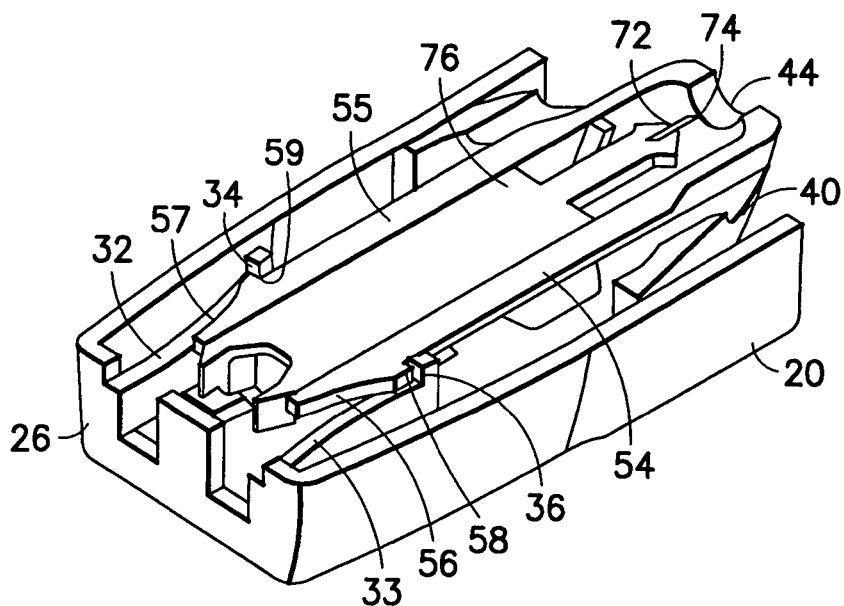
FIG. 10A is a perspective sectional view of the lancet device of FIG. 1 after use with the lancet structure in the final retracted position.
Figure 10B:
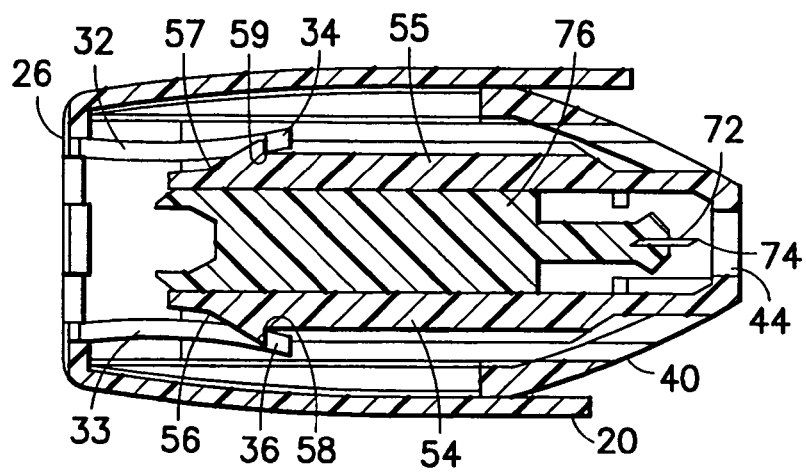
FIG. 10B is a cross-sectional view of the lancet device of FIG. 1 after use with the lancet structure in the final retracted position.

Once placed against the body, the user exerts a downwardly directed force on the rear housing body 20, forcing forward housing body 40 against that skin surface. In particular, the user applies a force against the finger grip indentation at the rearward end 26 of the rear housing body 20, thereby applying a force against the skin surface. Such force establishes an opposing external pressure force between the forward end of the forward housing body 40 and the rear housing body 20. Movement of forward housing body 40 within rear housing body 20 is initially prevented due to the interference engagement established through face edges 66 of forward housing body 40 abutting against the surface edges 65 of abutments 64 of rear housing body 20, as shown in FIG. 7E. As increased pressure is applied against the skin surface, the abutting surfaces between face edges 66 and surface edges 65 prevent movement of rear housing body 20 and forward housing body 40 with respect to each other until a pre-determined threshold pressure limit is reached. When additional force is applied against the skin surface beyond this pre-determined threshold limit, the interference engagement established through face edges 66 and surface edges 65 is overcome, as shown in FIG. 9C. This may be accomplished, for example, through a deformation of a portion the outer wall of forward housing body 40, thereby causing face edges 66 to move out of abutting engagement with the surface edges 65 of abutments 64, or may be accomplished by a deformation of the structure of abutments 64, thereby causing surface edges 65 of abutments 64 to move out of abutting engagement with face edges 66. Upon surpassing this pre-determined threshold pressure limit, the forward housing body 40 is caused to move axially or longitudinally within rear housing body 20. The corresponding guiding surfaces provided through legs 48 and rails 38 guide the forward housing body 40 axially through the rear housing body 20, ensuring proper axial alignment therebetween.

Such movement of the rear housing body 20 toward the forward housing body 40 causes the drive structure 30 to move lancet structure 70 with respect to forward housing body 40. In particular, as shown in FIGS. 9A-9B, when forward housing body 40 is pressed against the skin and rearward housing body 20 is forced toward the forward housing body 40, the protrusions 34, 35 and 36, 37 of fingers 32, 33 press against the corresponding abutment surfaces 84, 85, and 86, 87 of the lancet structure 70. The resilient stiff nature of fingers 32, 33 forcibly moves lancet structure 70 axially toward the forward end 42 of forward housing body 40 and toward the skin surface based on the force applied to the rear housing body 20. In embodiments such as that shown in FIG. 7C, drive post 98 may also act to move lancet structure 70 toward the forward end of forward housing body 40 toward the puncturing position. The puncturing end 74 of lancet structure 70 is driven by the user's force through forward housing body 40 to a puncturing position, in which puncturing end 74 of lancet 72 extends through the forward opening 44 through forward end 42 a sufficient distance to force the puncturing end 74 to puncture the skin surface. As such, the driving momentum which drives the lancet structure 70 and causes it to pierce the skin is established directly by the force of the user pressing against rear housing body 20, thereby transferring such force directly to the lancet structure 70 through the resilient fingers 32, 33. In this manner, the drive structure is sufficiently resilient or stiff so as to cause the lancet structure to puncture the skin without the drive structure collapsing, buckling, severing or otherwise deflecting based upon applied pressure alone, absent some physical structure within the housing to force the drive structure out of engagement with the lancet structure. It should be noted that the driving or positioning of the puncturing end 74 of lancet 72 into the patient's skin is not accomplished by the release or firing of a trigger-released spring-driven biasing element. It is therefore possible to have a lancet device that does not involve or require any pre-loaded spring to enable movement of the puncturing element towards the patient's skin during "firing" of the lancet device.

Such driving movement causes leaf springs 80, 82 to become increasingly compressed against their natural state during forward movement of lancet structure 70 toward the patient's skin, providing a bias between the forward end of the lancet structure 70 and the inner surface of the forward end of forward housing body 40. The structure of leaf springs 80, 82 is designed such that they are compressible, based upon the force of drive structure 30 driving lancet structure 70, to permit puncturing end 74 of lancet 72 to extend through forward opening 44.

Such driving movement also initiates a mechanism to release the interference engagement between the drive structure 30 and the lancet structure 70 during the movement of lancet structure 70 toward the forward housing body 40. In particular, during this driving movement, fingers 32, 33 are also somewhat flexible or deflectable so as to ride along and follow the contour of ramped surfaces 56, 57, respectively provided within forward housing body 40. This movement cams or deflects fingers 32, 33 radially outwardly with respect to the longitudinal axis of the lancet device 10 and the axis of movement of the lancet structure 70.

Continued axial movement of fingers 32, 33 causes further deflection, until fingers 32, 33 are deflected radially outwardly to a point at which protrusions 34, 35 and 36, 37 of fingers 32, 33 are released from abutting engagement with abutment surfaces 84, 85 and 86, 87. At this point, the leaf springs 80, 82 are compressed, but include sufficient resiliency to return to a less compressed state that further resembles their natural relaxed condition after the lancet structure 70 extends to the puncturing position. Accordingly, the leaf springs 80, 82 exert a biasing force between the forward end of the lancet structure 70 and the inner wall of forward end 42 of the forward housing body 40. Since the abutting engagement between protrusions 34, 35 and 36, 37 of fingers 32, 33 and abutment surfaces 84, 85 and 86, 87 is released and no longer permits transfer of force applied to the rear housing body 20 to the lancet structure 70, there is no driving force driving lancet structure 70 forward with respect to the patient's skin surface other than kinetic energy, and lancet structure 70 is therefore free to retract within housing 12 based on the stored energy of leaf springs 80, 82. In alternate embodiments of the invention, it is contemplated that the materials of the lancet device, and in particular the drives structure 30, may be designed to bend or break upon exertion of a load beyond a pre-determined tolerance level, thereby causing the drive structure 30 to move out of abutting engagement with the corresponding surfaces of lancet structure 70.

Moreover, during the axial movement of rear housing body 20 with respect to forward housing body 40, protrusions 34, 35, 36, 37 of fingers 32, 33 are deflected to a point at which they ride fully along the ramped surfaces 56, 57 and lock into notches 58, 59 at the forward end of ramped surfaces 56, 57. This interaction provides for interference engagement with fingers 32, 33 after deflection thereof, thereby locking the rear housing body 20 to the forward housing body 40, with lancet structure 70 retracted therein. The biasing force of leaf springs 80, 82 maintains the lancet structure 70 disposed within the housing 12 with puncturing end 74 shielded therein, preventing further movement of lancet structure 70 to the puncturing position.

Moreover, with protrusions 34, 35, 36, 37 of fingers 32, 33 locked within the respective notches 58, 59, they are fixed in a position out of any interference engagement with the lancet structure 70, and the rear housing body 20 is fixed from further axial movement relative to the forward housing body 40. The lancet device 10 is therefore safely protected from re-use and may be properly discarded, such as in an appropriate medical waste container.

As noted above, initial activation of the lancet device 10 is based on the amount of force applied between the rear housing body 20 and the forward housing body 40 when the lancet device 10 is pressed against the patient's skin surface. This threshold limit of pressure is a pre-determined value, and is desirably based upon the amount of force which is required to be applied between the rear housing body 20 and the forward housing body 40 which will result in a series of actions, including movement of the lancet structure entirely through the forward housing body 40, compression of leaf springs 80, 82 against their natural state and deflection of the fingers 32, 33 radially outwardly, as well as the force required to pierce the patient's skin. In certain applications, it is contemplated that the pre-determined value for this threshold limit is about 1 pound-force (lbf) to about 3 lbf of force. With such a pre-determined threshold limit of pressure, lancet device 10 is fully activated in one swift movement, in that once sufficient pressure is achieved to overcome the threshold limit based upon the pressure applied between the rear housing body 20 and the forward housing body 40, the amount of pressure required to continue momentum which causes activation of the lancet device 10, i.e., movement of lancet device 10 to achieve puncturing of the skin followed by retraction of the lancet, is already being applied between the respective forward and rearward bodies of the device. Accordingly, exposure of the puncturing element of the lancet is caused when the frictional interference engagement between the rear housing body 20 and the forward housing body 40 is overcome, based upon the force applied between the rear housing body 20 and forward housing body 40 to establish movement therebetween. As such, the lancet device is inertia-powered, and achieves complete activation and retraction in a single moment of applied pressure above this threshold limit.

While activation of the device is described herein in a stepwise fashion, it is noted that puncturing of the skin and retraction of the lancet occur almost instantaneously due to the design of the device and the tolerance of the materials. As such, while it is the actual pressure applied by the user which is directly transferred to force the lancet to puncture the skin surface, the retraction is also based upon such application of force, in that the pressure applied expands or deflects the element transferring the force, i.e., the drive structure, to release the lancet and permit retraction through the retainer element. Therefore activation of the device including piercing and retraction occur almost simultaneously in a single operation. The lancet device of the present invention therefore provides an effective and economical structure which is easy to manufacture and assemble and which is safely protected from re-use.

While the present invention is described with reference to preferred embodiments of the lancet device, those skilled in the art may make modifications and alterations to the present invention without departing from the scope and spirit of the invention. Accordingly, the above detailed description is intended to be illustrative rather than restrictive. The invention is defined by the appended claims, and all changes to the invention that fall within the meaning and range of equivalency of the claims are to be embraced within their scope.

The invention claimed is:

1. A lancet device comprising:
    a lancet structure comprising a puncturing element;
    a housing comprising a rear housing portion and a forward housing portion longitudinally movable with respect to each other and in initial abutting interference engagement with one another in a lancing direction of user force application; and
    a lancet retention member for maintaining the puncturing element within the housing;
    wherein longitudinal movement of the rear housing portion with respect to the forward housing portion overcomes the initial abutting interference engagement and the rear housing portion engages the lancet structure thereby causing the lancet structure to move substantially in conjunction with the rear housing portion to expose the puncturing element through the forward housing portion;
    wherein upon further longitudinal movement of the rear housing portion with respect to the forward housing portion, the rear housing portion disengages from the lancet structure and the lancet retention member retracts the puncturing element within the forward housing portion; and
    wherein the rear housing portion includes a locking structure for locking engagement with the forward housing portion as a result of the longitudinal movement, thereby preventing re-exposure of the puncturing element through the forward housing portion and locking the front housing portion with the rear housing portion.

2. The lancet device of claim 1, wherein exposure of the puncturing element is caused when the initial abutting interference engagement is overcome by a sufficient inertial force applied to the housing to enable the longitudinal movement.

3. The lancet device of claim 2, wherein the sufficient inertial force for enabling said longitudinal movement is greater than 1 lbf.

4. The lancet device of claim 1, wherein the lancet structure is longitudinally movable with respect to the rear housing portion after exposure of the puncturing element.

5. The lancet device of claim 1, wherein the rear housing portion is external to the forward housing portion.

6. The lancet device of claim 1, wherein the rear housing portion further comprises structure for abutting engagement with the lancet structure, and wherein said longitudinal movement causes the lancet structure to move substantially in conjunction with the rear housing portion based on such abutting engagement.

7. The lancet device of claim 6, wherein the forward housing portion includes a guiding surface which engages with the abutting engagement structure of the rear housing portion, and wherein said longitudinal movement causes the abutting engagement structure to engage the guiding surface, thereby disengaging the structure from abutting engagement with the lancet structure during exposure of the puncturing element.

8. The lancet device of claim 7, wherein the abutting engagement structure of the rear housing portion comprises at least one resiliently deflectable finger extending from the rear housing portion and wherein the guiding surface of the forward housing portion comprises at least one corresponding ramped surface, the at least one resiliently deflectable finger sliding along the at least one corresponding ramped surface and deflecting radially outwardly upon said longitudinal movement.

9. The lancet device of claim 8, wherein the guide surface of the forward housing portion comprises a ramped surface having a notch for interference engagement with a protrusion of the abutting engagement structure of the rear housing portion upon said longitudinal movement, said interference engagement establishing said locking structure, thereby preventing reuse of the lancet device.

10. The lancet device of claim 1, wherein the lancet retention member comprises a spring member biasing the lancet structure away from the forward end of the forward housing portion.

11. The lancet device of claim 10, wherein the spring member comprises at least one leaf spring integral with the lancet structure.

12. The lancet device of claim 1, further comprising a lancet cover removably covering the puncturing element of the lancet structure.

13. The lancet device of claim 1, wherein the rear housing portion comprises an abutment structure and the forward housing portion comprises a corresponding face edge, the abutment structure and the corresponding face edge engage to form the initial abutting interference engagement between the rear housing portion and the forward housing portion.

14. A lancet device comprising:
    a lancet structure comprising a puncturing element;
    a housing comprising a first housing portion and a second housing portion axially movable with respect to each other and in initial abutting interference engagement with one another in a lancing direction of user force application, the first housing portion including structure for abutting engagement with a corresponding abutment surface of the lancet structure, the second housing portion including a guiding surface adapted for engagement with the abutting structure of the first housing portion during axial movement of the first housing portion and the second housing portion with respect to each other; and
    a lancet retention member for maintaining the puncturing element of the lancet structure within the housing;
    wherein axial movement of the first housing portion with respect to the second housing portion overcomes the initial abutting interference engagement and causes the abutting structure of the first housing portion to move the lancet structure to a position wherein the puncturing element extends through a forward end of the second housing portion due to the abutting engagement between the abutting structure and the lancet structure, and causes the abutting structure to engage the guiding surface of the second housing portion to disengage the abutting structure from the corresponding abutment surface of the lancet structure upon extension of the puncturing element through the forward end of the second housing portion, thereby permitting the lancet retention member to retract the puncturing element within the forward end of the second housing portion; and
    wherein one of the first housing portion and second housing portion includes a locking structure for locking engagement with the other of the first housing portion and second housing portion as a result of said axial movement, thereby preventing re-exposure of the puncturing element through the second housing portion and locking the first housing portion with the second housing portion.

15. The lancet device of claim 14, wherein the initial abutting interference engagement prevents said axial movement of the first housing portion with respect to the second housing portion until the initial abutting interference engagement is overcome by a sufficient inertial force applied to the housing to overcome the initial abutting interference engagement and enable said axial movement and the sufficient inertial force comprises a pre-determined force value.

16. The lancet device of claim 15, wherein the pre-determined force value is greater than 1 lbf.

17. The lancet device of claim 15, wherein the pre-determined force value exceeds a minimum force value which is required to cause said axial movement of the first housing portion with respect to the second housing portion, which thereby causes the puncturing element to extend through a forward end of the second housing portion, and causes the abutting structure to engage the guiding surface of the second housing portion to disengage the abutting structure from the abutment surface upon extension of the puncturing element through the forward end of the second housing portion, thereby permitting the lancet retention member to retract the puncturing element within the forward end of the second housing portion.

* * * * *